United States Patent [19]
Adachi et al.

[11] 4,085,114
[45] Apr. 18, 1978

[54] 1,2-BENZOISOXAZOLE DERIVATIVES AND THE PRODUCTION THEREOF

[75] Inventors: Ikuo Adachi; Motohiko Ueda, both of Suita; Sadatoshi Kimoto, Kusatsu, all of Japan

[73] Assignee: Shionogi & Co., Ltd., Osaka, Japan

[21] Appl. No.: 713,044

[22] Filed: Aug. 9, 1976

[30] Foreign Application Priority Data

Sep. 9, 1975 United Kingdom ............... 37132/75

[51] Int. Cl.$^2$ ........................................... C07D 261/20
[52] U.S. Cl. .............................. 260/307 DA; 424/272
[58] Field of Search ................................ 260/307 DA

[56] References Cited

PUBLICATIONS

Vitali et al., C.A.72,31781w, (1970), Abstract of Ger. Offen., 1,915,664 of 10-9-69.

*Primary Examiner*—Raymond V. Rush
*Attorney, Agent, or Firm*—Wenderoth, Lind & Ponack

[57] ABSTRACT

3-Substituted-4-(5, 6, or 7)-(2-hydroxy-3-substituted aminopropoxy)-1,2-benzisoxazoles synthesized from 3-substituted-4 (5, 6, or 7)-(2,3-epoxypropoxy)-1,2-benzisoxazoles with a primary amine showing β-blocking activity with low toxicity.

7 Claims, No Drawings

1,2-BENZOISOXAZOLE DERIVATIVES AND THE PRODUCTION THEREOF

This invention provides novel 1,2-benzisoxazole derivatives and its pharmaceutically acceptable salts having β-blocking activity. Furthermore, it relates to a process for their production.

The novel compounds of this invention are 3-substituted-4 (5, 6, or 7)-(2-hydroxy-3-substituted aminopropoxy)-1,2-benzisoxazoles of the general formula:

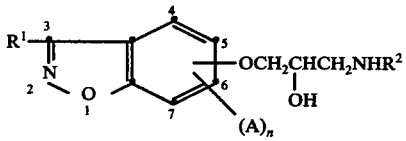

wherein $R^1$ is $C_{1-4}$ alkyl or phenyl;
$R^2$ is isopropyl, tert-butyl, 3,4-dimethoxyphenethyl, or phenoxyethyl;
A is hydrogen, methyl, allyl, acetyl, acetylamino, cyclohexylureido, or phenylureido; and
n is 1 or 2;
with a proviso that, when A is not hydrogen, the group A is located at 5 or 7 position,
and the pharmaceutically acceptable acid-addition salts thereof.

The term $C_{1-4}$ alkyl, as used herein, refers to both straight and branched aliphatic radicals of one to four carbon atoms including methyl, ethyl, propyl, isopropyl, butyl, isobutyl, and the like. The preferred group $R^1$ is $C_{1-3}$ alkyl and the most preferably is methyl.

Among the groups for $R^2$, isopropyl and tert-butyl are preferred. The most preferred is tert-butyl.

The group

may be located at 4, 5, 6, or 7 position of the 1,2-benzisoxazole ring, the preferred position being 4 and 7 and the most preferred being 4.

The 1,2-benzisoxazole ring may be substituted at 5 or 7 position. The substituents are methyl, allyl, acetyl, acetylamino, cyclohexylureido and phenylureido. Furthermore, the ring may be substituted by two of the same substituents at 5 and 7 positions. The substituents are as noted above.

As illustrative of the objective compound of the formula [I] are:
3-methyl-4-(2-hydroxy-3-isopropylaminopropoxy)-1,2-benzisoxazole,
3-methyl-4-(2-hydroxy-3-isopropylaminopropoxy)-7-acetylamino-1,2-benzisoxazole,
3,5-dimethyl-4-(2-hydroxy-3-isopropylaminopropoxy)-1,2-benzisoxazole,
3-methyl-4-(2-hydroxy-3-isopropylaminopropoxy)-5-allyl-1,2-benzisoxazole,
3,7-dimethyl-4-(2-hydroxy-3-isopropylaminopropoxy)-1,2-benzisoxazole,
3-methyl-4-(2-hydroxy-3-isopopylaminopropoxy)-5,7-diacetyl-1,2-benzisoxazole,
3-methyl-4-(2-hydroxy-3-tert-butylaminopropoxy)-1,2-benzisoxazole,
3-methyl-4-(2-hydroxy-3-tert-butylaminopropoxy)-7-acetylamino-1,2-benzisoxazole,
3-methyl-4-(2-hydroxy-3-tert-butylaminopropoxy)-7-cyclohexylureido-1,2-benzisoxazole,
3-methyl-4-(2-hydroxy-3-tert-butylaminopropoxy)-7-phenylureido-1,2-benzisoxazole,
3-methyl-4-(2-hydroxy-3-tert-butylaminopropoxy)-5-acetyl-1,2-benzisoxazole,
3-methyl-4-(2-hydroxy-3-tert-butylaminopropoxy)-7-acetyl-1,2-benzisoxazole,
3-methyl-4-(2-hydroxy-3-tert-butylaminopropoxy)-5-allyl-1,2-benzisoxazole,
3,5-dimethyl-4-(2-hydroxy-3-tert-butylaminopropoxy)-1,2-benzisoxazole,
3,5,7-trimethyl-4-(2-hydroxy-3-tert-butylaminopropoxy)-1,2-benzisoxazole,
3-methyl-4-[2-hydroxy-3-(3,4-dimethoxyphenethylamino)propoxy]-1,2-benzisoxazole,
3,7-dimethyl-4-[2-hydroxy-3-(3,4-dimethoxyphenethylamino)propoxy]-1,2-benzisoxazole,
3-methyl-4-(2-hydroxy-3-phenoxyethylaminopropoxy)-1,2-benzisoxazole,
3-ethyl-4-(2-hydroxy-3-isopropylaminopropoxy)-5-methyl-1,2-benzisoxazole,
3-ethyl-4-(2-hydroxy-3-isopropylaminopropoxy)-7-cyclohexylureido-1,2-benzisoxazole,
3-ethyl-4-(2-hydroxy-3-tert-butylaminopropoxy)-1,2-benzisoxazole,
3-ethyl-4-(2-hydroxy-3-tert-butylaminopropoxy)-7-acetyl-1,2-benzisoxazole,
3-ethyl-4-[2-hydroxy-3-(3,4-dimethoxyphenethylamino)propoxy]-1,2-benzisoxazole,
3-propyl-4-(2-hydroxy-3-isopropylaminopropoxy)-1,2-benzisoxazole,
3-propyl-4-(2-hydroxy-3-isopropylaminopropoxy)-7-allyl-1,2-benzisoxazole,
3-propyl-4-(2-hydroxy-3-tert-butylaminopropoxy)-1,2-benzisoxazole,
3-propyl-4-[2-hydroxy-3-(3,4-dimethoxyphenethylamino)propoxy]-5,7-dimethyl-1,2-benzisoxazole,
3-propyl-4-(2-hydroxy-3-phenoxyethylaminopropoxy)-1,2-benzisoxazole,
3-isopropyl-4-(2-hydroxy-3-isopropylaminopropoxy)-1,2-benzisoxazole,
3-isopropyl-4-(2-hydroxy-3-tert-butylaminopropoxy)-5-acetyl-1,2-benzisoxazole,
3-butyl-4-(2-hydroxy-3-isopropylaminopropoxy)-1,2-benzisoxazole,
3-butyl-4-(2-hydroxy-3-isopropylaminopropoxy)-7-cyclohexylureido-1,2-benzisoxazole,
3-butyl-4-(2-hydroxy-3-tert-butylaminopropoxy)-5-methyl-1,2-benzisoxazole,
3-butyl-4-[2-hydroxy-3-(3,4-dimethoxyphenethylamino)propoxy]-1,2-benzisoxazole,
3-butyl-4-(2-hydroxy-3-phenoxyethylaminopropoxy)-1,2-benzisoxazole,
3-isobutyl-4-(2-hydroxy-3-isopropylaminopropoxy)-1,2-benzisoxazole,
3-isobutyl-4-(2-hydroxy-3-tert-butylaminopropoxy)-1,2-benzisoxazole,
3-isobutyl-4-(2-hydroxy-3-tert-butylaminopropoxy)-7-acetylamino-1,2-benzisoxazole,
3-isobutyl-4-[2-hydroxy-3-(3,4-dimethoxyphenethylamino)propoxy]-1,2-benzisoxazole,
3-isobutyl-4-(2-hydroxy-3-phenoxyethylaminopropoxy)-7-allyl-1,2-benzisoxazole, 3-phenyl-4-(2-hydroxy-3-isopropylaminopropoxy)-1,2-benzisoxazole,
3-phenyl-4-(2-hydroxy-3-tert-butylaminopropoxy)-1,2-benzisoxazole,
3-phenyl-4-(2-hydroxy-3-tert-butylaminopropoxy)-5,7-diacetyl-1,2-benzisoxazole,
3-phenyl-4-(2-hydroxy-3-phenoxyethylaminopropoxy)-1,2-benzisoxazole,
3-methyl-5-(2-hydroxy-3-isopropylaminopropoxy)-1,2-benzisoxazole,
3-methyl-5-(2-hydroxy-3-tert-butylaminopropoxy)-1,2-benzisoxazole,
3,7-dimethyl-5-(2-hydroxy-3-tert-butylaminopropoxy)-1,2-benzisoxazole,
3-methyl-5-[2-hydroxy-3-(3,4-dimethoxyphenethylamino)propoxy]-1,2-benzisoxazole,
3-methyl-5-(2-hydroxy-3-phenoxyethylaminopropoxy)-1,2-benzisoxazole,
3-ethyl-5-(2-hydroxy-2-isopropylaminopropoxy)-1,2-benzisoxazole,
3-ethyl-5-(2-hydroxy-3-tert-butylaminopropoxy)-1,2-benzisoxazole,
3-propyl-5-(2-hydroxy-3-tert-butylaminopropoxy)-1,2-benzisoxazole,
3-isopropyl-5-(2-hydroxy-3-isopropylaminopropoxy)-1,2-benzisoxazole,
3-butyl-5-[2-hydroxy-3-(3,4-dimethoxyphenethylamino)propoxy]-1,2-benzisoxazole,
3-phenyl-5-(2-hydroxy-3-isopropylaminopropoxy)-1,2-benzisoxazole,
3-phenyl-5-(2-hydroxy-3-tert-butylaminopropoxy)-1,2-benzisoxazole,
3-methyl-6-(2-hydroxy-3-isopropylaminopropoxy)-1,2-benzisoxazole,
3,5-dimethyl-6-(2-hydroxy-3-isopropylaminopropoxy)-1,2-benzisoxazole,
3-methyl-5-allyl-6-(2-hydroxy-3-isopropylaminopropoxy)-1,2-benzisoxazole,
3-methyl-6-(2-hydroxy-3-tert-butylaminopropoxy)-1,2-benzisoxazole,
3-methyl-6-(2-hydroxy-3-tert-butylaminopropoxy)-7-allyl-1,2-benzisoxazole,
3-methyl-5-acetyl-6-(2-hydroxy-3-tert-butylaminopropoxy)-1,2-benzisoxazole,
3-methyl-6-[2-hydroxy-3-(3,4-dimethoxyphenethylamino)propoxy]-1,2-benzisoxazole,
3-ethyl-6-(2-hydroxy-3-tert-butylaminopropoxy)-1,2-benzisoxazole,
3-propyl-5-acetylamino-6-(2-hydroxy-3-isopropylaminopropoxy)-1,2-benzisoxazole,
3-propyl-5-phenylureido-6-(2-hydroxy-3-tert-butylaminopropoxy)-1,2-benzisoxazole,
3-isopropyl-6-(2-hydroxy-3-tert-butylaminopropoxy)-1,2-benzisoxazole,
3-butyl-6-(2-hydroxy-3-tert-butylaminopropoxy)-1,2-benzisoxazole,
3-phenyl-6-(2-hydroxy-3-tert-butylaminopropoxy)-1,2-benzisoxazole,
3-methyl-7-(2-hydroxy-3-isopropylaminopropoxy)-1,2-benzisoxazole,
3,5-dimethyl-7-(2-hydroxy-3-isopropylaminopropoxy)-1,2-benzisoxazole,
3-methyl-7-(2-hydroxy-3-tert-butylaminopropoxy)-1,2-benzisoxazole,
3-methyl-7-[2-hydroxy-3-(3,4-dimethoxyphenethylamino)propoxy]-1,2-benzisoxazole,
3-methyl-7-(2-hydroxy-3-phenoxyethylaminopropoxy)-1,2-benzisoxazole,
3-ethyl-7-(2-hydroxy-3-isopropylaminopropoxy)-1,2-benzisoxazole,
3-ethyl-7-[2-hydroxy-3-(3,4-dimethoxyphenethylamino)propoxy]-1,2-benzisoxazole,
3-propyl-7-(2-hydroxy-3-tert-butylaminopropoxy)-1,2-benzisoxazole,
3-propyl-7-(2-hydroxy-3-phenoxyethylaminopropoxy)-1,2-benzisoxazole,
3-isopropyl-7-(2-hydroxy-3-isopropylaminopropoxy)-1,2-benzisoxazole,
3-butyl-7-(2-hydroxy-3-tert-butylaminopropoxy)-1,2-benzisoxazole,
3-isobutyl-7-(2-hydroxy-3-tert-butylaminopropoxy)-1,2-benzisoxazole,
3-phenyl-7-(2-hydroxy-3-tert-butylaminopropoxy)-1,2-benzisoxazole, The preferred compounds of formula I are 3-$C_{1-4}$ alkyl-4 (5, 6, or 7)-(2-hydroxy-3-substituted aminopropoxy)-1,2-benzisoxazoles, especially the 3-$C_{1-4}$ alkyl-4 (or 7)-(2-hydroxy-3-substituted aminopropoxy)-1,2-benzisoxazoles. More preferred are the 3-methyl-4 (or 7)-(2-hydroxy-3-substituted aminopropoxy)-1,2-benzisoxazoles. The most preferred are the 3-methyl-4-(2-hydroxy-3-substituted aminopropoxy)-1,2-benzisoxazole, particularly 3-methyl-4-(2-hydroxy-3-isopropyl (or tert-butyl)aminopropoxy)-1,2-benzisoxazole.

Some 1,2-benzisoxazole ethers are disclosed to act on the cardio-circulatory system and the respiratory organ in German open to public inspection application No. 1,915,644 published on Oct. 9, 1969. The compounds are 1,2-benzisoxazole derivatives substituted by a primary or secondary amino-ethoxy (or-propoxy) group at 3 position. The compounds are obviously different from the compounds of the present invention in substituents.

The compounds of the formula [I] can be produced by some different methods, one of which starts with 3-substituted-4 (5, 6, or 7)-hydroxy-1,2-benzisoxazoles. The process may be shown by the following reaction scheme:

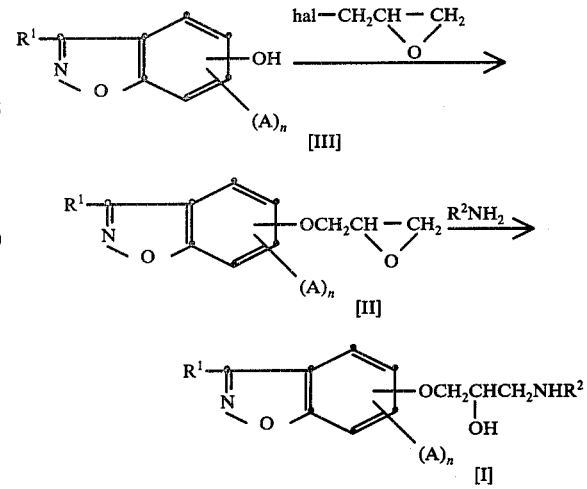

wherein hal is halogen and $R^1$, $R^2$, A and $n$ are each as defined above.

In the present process, a compound of the formula [III], a 3-substituted-4 (5, 6, or 7)-hydroxy-1,2-benzisoxazole is condensed with an epihalohydrin (e.g. epibromohidrin or epichlorohydrin) preferrably in the presence of a base such as sodium hydride, an alkali metal hydroxide (e.g. sodium hydroxide or potassium hydroxide), an alkali metal alkoxide (e.g. potassium methoxide, sodium ethoxide), an alkali metal carbonate (e.g. sodium carbonate) and the like. The reaction may be effected in a suitable solvent (e.g. water, methanol, ethanol, benzene, toluene, or dimethylformamide or a mixture thereof) at a temperature of from room temperature to about 80° C.

The resultant epoxide [II] is then condensed with a primary amine, i.e. isopropylamine, tert-butylamine, 3,4-dimethoxyethylamine, or phenoxyethylamine. The reaction can be effected at a temperature of from room temperature to the reflux temperature of the reaction mixture, ca. 30°–110° C. Solvent is optionally used. The suitable solvents are alcohols (e.g. methanol or ethanol), ethers (e.g. ether or tetrahydrofuran), hydrocarbons (e.g. benzene, toluene, or xylene), dimethylformamide and the like. They are used singly or as a mixture.

Some of the starting compounds [III] used in the present process are known; 3-methyl-4-hydroxy-1,2-benzisoxazole is described by P. Crabbe et al. (J. Chem. Soc., 2220 (1973)); and 3-methyl-5-hydroxy-1,2-benzisoxazole is by H. Lindemann et al. (Ann. Chem., 456, 284 (1927)). Further, 3-methyl-6-hydroxy-1,2-benzisoxazole can be obtained by hydrolysis of the corresponding acetyl derivative with a base as shown by S. S. Kumari et al. (Ind. J. Chem., 11, 541 (1973)). The 7-hydroxy derivative can be prepared by Lindemann's method shown in the reference mentioned above from 2,3-dihydroxyacetophenone acetoxime. The other starting compound [III] can similarly be produced by the method shown in the above-described references.

The compounds of the formula [I] form pharmaceutically acceptable acid-addition salts with a variety of inorganic or organic acids. Such salts include, for example, the hydrochloride, hydrobromide, hydroiodide, sulfate, nitrate, phosphate, thiocyanate, carbonate, acetate, propionate, oxalate, succinate, maleate, tartarate, citrate, benzoate, salicylate and phthalate salts.

The compounds of this invention exhibit β-blocking activity. The pharmacological activity may be examined by the following methods, the results being shown in Table 1.

EXPERIMENT

A. Methods:

Guinea-pigs of either sex, weighing between 400 – 700 g each, were killed by a sharp blow on the head. Their atria and trachea were quickly excised and freed of excess tissues.

1. β-Blocking activities in the isolated atria:

The isolated atria were mounted in a 30 ml organ bath filled with Krebs-Ringer-bicarbonate solution, which was constantly bubbled with a gas mixture of 95% oxygen and 5% carbon dioxide at 30° C. Spontaneous contractions of the atria were isometrically recorded on the polygraph (RM-150, Nihon Kohden Kogyo) by mean of a F-D pick-up (N. K. K.) and the number of contractions in one minute was recorded on the home-made pulse counter triggered by the atrial contractions. After the repeated administration of isoproterenol ($5 \times 10^{-10}$ g/ml) constantly induced marked positive inotropic and chronotropic responses, the inhibitory effects of the benzisoxazole derivatives on the isoproterenol responses were compared with those of propranolol. The benzisoxazole derivatives and propranolol were preincubated with the atria for 10 minutes before the administration of isoproterenol. The fifty percent inhibitory concentration of the benzisoxazole derivatives and propranolol on the positive inotropic effect of isoproterenol ($IC_{50}$) were graphically determined.

2. β-Blocking activities in the isolated trachea:

The isolated tracheal tube was cut into round slices consisting of two or three cartilage rings. After 8 such rings were linked, side by side, with an instant adhesive (Aron Alpha, Toa Gosei Kagaku), they were mounted in a 30 ml organ bath filled with Krebs-Ringer-bicarbonate solution, which was constantly bubbled with a gas mixture of 95% oxygen and 5% carbon dioxide at 37° C.

The isotonic relaxation of the tracheal chain by the administration of isoproterenol was recorded on the kymographic paper. After the repeated administration of isoproterenol ($10^{-8}$ g/ml) induced constant relaxations, the inhibitory effects of the benzisoxazole derivatives on the isoproterenol responses were compared with those of propranolol. The benzisoxazole derivatives and propranolol were preincubated with the tracheal chain for 1 hour before the administration of isoproterenol. The fifty percent inhibitory concentration of the benzisoxazole derivatives and propranolol on the relaxation of tracheal chain by isoproterenol ($IC_{50}$) were graphically determined.

3. $LD_{50}$ of benzisoxazole derivatives in mice:

Female DS mice weighing about 20 g were employed. The $LD_{50}$ values of intravenously administered benzisoxazole derivatives were calculated by the Up and Down method of Brownlee (J. Am. Stat. As., 48, 262–277, 1953).

B. Result:

Table I

| Test Compound | 1. Atria (g/ml) | 2. Trachea (g/ml) | 3. $LD_{50}$ (mg.Kg) i.v. |
|---|---|---|---|
| 3-Methyl-4-(2-hydroxy-3-tert-butylamino-propoxy)-1,2-benz-isoxazole | $7.9 \times 10^{-9}$ | $1.1 \times 10^{-9}$ | 41.8 |
| 3-Methyl-4-(2-hydroxy-3-isopropylamino-propoxy)-1,2-benz-isoxazole | $2.5 \times 10^{-8}$ | — | 45.0 |
| Propranolol | $1.2 \times 10^{-8}$ | $2.8 \times 10^{-9}$ | 30.7 | i.v.: Intravenous injection
—: No experiment

As shown in Table 1, the test compounds show β-blocking activity in atria with low toxicity. The compounds of this invention other than shown above also exhibit β-blocking activity. Thus, the compound of this invention are useful in the treatment of arrhythmias and for the prevention angina pectoris. Furthermore, they may be used to the treatment of hypertension. This invention includes a method for such treatment or prevention in animals, which method comprises administering an effective amount of a compound, salt, formulation or composition in accordance with the invention.

The compounds of this invention can be administered orally or by injection. The compounds may be employed in combination with one or more adjuvants suited to the particular route of administration. Thus, in the case of oral administration, the compound may be modified with pharmaceutical diluents or carriers such as lactose, sucrose, starch powder, cellulose, talc, magnesium stearate, magnesium oxide, calcium sulfate, acacia powder, gelatin, sodium alginate, sodium benzoate and stearic acid. Such compositions can be formulated as tablets or enclosed in capsules for convenient administration. An injectable solution can be prepared with, e.g. distilled water, physiological salt solution or Ringer's solution.

Thus, the invention provides a pharmaceutical or veterinary formulation which comprises a compound or salt in accordance with the invention in an appropriate state of purity and in unit dosage form. The invention further includes a pharmaceutical or veterinary composition which comprises a compound or salt in accordance with the invention and a pharmaceutically acceptable or veterinarily acceptable, respectively, diluent, carrier or excipient.

The present compositions may be in unit dosage form if desired.

The present invention also includes a method for inducing a β-blocking activity in an animal, which method comprises administering to the animal an effective amount of a compound, salt, formulation or composition in accordance with the invention.

The present compounds may be orally administered in a dosage of from 3–300 mg a day and intravenously administered in a dosage of from 0.1–50 mg at a time.

The invention will now be further described and illustrated by way of the following examples.

EXAMPLE 1

3-Methyl-4-(3-isopropylaminopropoxy)-1,2-benzisoxazole

A mixture of 3-methyl-4-(2,3-epoxypropoxy)-1,2-benzisoxazole (4 mmole), isopropylamine (2 ml) and methanol (5 ml) is heated at 70°–80° C for 2 hours in a sealed tube. The methanol and excess amine are evaporated. The residue is recrystallized from benzene-hexane to give the objective compound as colorless plates melting at 108°–109° C (yield 89.6%). IR $\nu_{max}^{Nujol}$ cm$^{-1}$ 3300, 2880, 1618.

The product is converted into the hydrochloride salt with alcoholic hydrochloric acid in ether and recrystallized from ethanol-ether to give colorless plates melting at 183°–184° C.

Anal. Calcd. for $C_{14}H_{20}N_2O_3 \cdot HCl$: C, 55.91; H, 7.04; N, 9.31 Found: C, 55.79; H, 7.07; N, 9.30 IR $\nu_{max}^{Nujol}$ cm$^{-1}$ 3360, 2700, 1608.

Preparation of 3-methyl-4-(2,3-epoxypropoxy)-1,2-benzisoxazole ..... To a solution of sodium hydroxide (0.7 g, 17 mmole) in methanol (40 ml) is gradually added 3-methyl-4-hydroxy-1,2-benzisoxazole (15 mmole) and then epichlorohydrin (20 ml). The mixture is stirred at room temperature for 18 hours. After evaporation of methanol and excess epichlorohydrin under reduced pressure, the residue is extracted with chloroform. The extract is washed with a dilute solution of sodium hydroxide and water, dried over magnesium sulfate, and evaporated. The residue is subjected to column chromatography using silica gel and eluted with chloroform. The solvent is evaporated. The residue is recrystallized from isopropyl ether to give 3-methyl-4-(2,3-epoxypropoxy)-1,2-benzisoxazole as colorless prisms melting at 51°–53° C (yield 95.0%).

Anal. Calcd. for $C_{11}H_{11}NO_3$: C, 64.38; H, 5.40; N, 6.83 Found: C, 64.57; H, 5.36; N, 6.63 IR $\nu_{max}^{Nujol}$ cm$^{-1}$ 1611, 1255

Examples 2–8

A similar treatment as in Example 1 gives the compounds set out in Table 2:

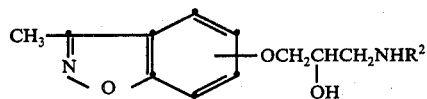

Table 2

| Ex. No. | a | R² | Yield | M.P. (° C) | b | c | IR $\nu_{max}^{Nujol}$ cm$^{-1}$ | | Formula Anal. (%) Calcd. Found |
|---|---|---|---|---|---|---|---|---|---|
| | | | | | | | Free Base / Hydrochloride salt | | C   H   N |
| 2 | 4 | t-Bu | 68.2 | 120–21 | Pl | D | 3270 | 2800 1618 | $C_{15}H_{22}N_2O_3 \cdot HCl$ |
| | | | | 232–234 | Pr | B | 3270 | 2600 1618 | 57.23 7.36 8.90 57.29 7.27 9.05 |
| 3 | 5 | i-Pr | 77.4 | 108–110 | N | D | 3260 | 2720 1623 | $C_{14}H_{20}N_2O_3 \cdot HCl$ |
| | | | | 133–135 | Pr | C | 3280 | 2600 1590 | 55.91 7.04 9.31 56.02 7.03 9.42 |
| 4 | 5 | t-Bu | 73.5 | 112–114 | N | D | 3300 | 2900 1618 | $C_{15}H_{22}N_2O_3 \cdot HCl$ |
| | | | | 188–189 | Pr | B | 3360 | 2680 1620 | 57.23 7.36 8.90 56.68 7.39 8.85 |
| 5 | 6 | i-Pr | 99.3 | 116–117 | N | D | 3242 | 2800 1623 | $C_{14}H_{20}N_2O_3 \cdot HCl$ |
| | | | | 172–173 | Pr | C | 3360 | 2600 1620 | 55.91 7.04 9.31 56.08 7.13 9.37 |
| 6 | 6 | t-Bu | 84.7 | 110–112 | N | D | 3250 | 2800 1620 | $C_{15}H_{22}N_2O_3 \cdot HCl$ |
| | | | | 184–186 | Pr | B | 3250 | 2600 1621 | 57.23 7.36 8.90 57.42 7.42 9.04 |
| 7 | 7 | i-Pr | 82.3 | 75–77 | Pr | A | 3250 | 2800 1607 | $C_{14}H_{20}N_2O_3 \cdot HCl$ |
| | | | | 227–229 | Pr | B | 3210 | 2680 1605 | 55.91 7.04 9.31 56.20 7.07 9.35 |
| 8 | 7 | t-Bu | 97.7 | 92–94 | Pr | D | 3250 | 2790 1607 | $C_{15}H_{22}N_2O_3 \cdot HCl$ |
| | | | | 213–215 | Pr | B | 3280 | 2760 1603 | 57.23 7.36 8.90 57.22 7.47 9.06 |

Note:
Ex. No. : Example number
a : The position of the 1,2-benzisoxazole ring substituted by the group —OCH₂CHCH₂NHR²
                                                                              |
                                                                             OH
b : Appearance of the compound,

Table 2-continued

| Ex. No. | a | R² | Yield | M.P. (°C) Free Base Hydrochloride salt | b | c | IR $\nu_{max}^{Nujol}$ cm⁻¹ | Formula | Anal. (%) Calcd. Found C H N |
|---|---|---|---|---|---|---|---|---|---|

Pl = colorless plates, Pr = colorless prisms,
N = colorless needles,
c : Recrystallization solvent,
  A = isopropyl ether, B = ethanol, C = ethanol-ether,
  D = benzene-hexane
t-Bu: tert-butyl
i-Pr: isopropyl

EXAMPLES 9–13

A mixture of 3-methyl-4 (5, 6, or 7)-(2,3-epoxy-propoxy)-1,2-benzisoxazole (308 mg, 1.5 mmole), 3,4-dimethyoxyphenethylamine (0.33 g, 1.8 mmole) or β-phenoxyethylamine (206 mg, 1.5 mmole), and methanol (10 ml) is refluxed for 2 hours. The methanol is evaporated. The residue is recrystallized from a suitable solvent to give the compounds set out in Table 3:

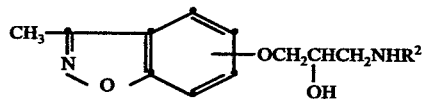

EXAMPLES 14–29

A similar treatment as in Example 1 or Examples 9–13 gives the following compounds set out in Table 4:

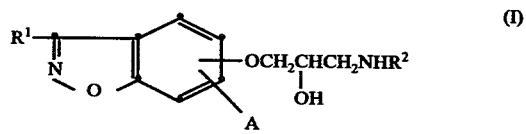

(I)

Table 3

| Ex. No. | a | R² | Yield | M.P. (°C) Free Base Oxalate* or HCl** salt | b | c | IR $\nu_{max}^{Nujol}$ cm⁻¹ | Formula Anal. (%) Calcd. Found C H N |
|---|---|---|---|---|---|---|---|---|
| 9 | 4 | DMPᵈ | 36.4 | 105–106 | N | D | 3250 2900 1607 | $C_{23}H_{28}N_2O_9$* |
|   |   |     |      | *184–186 | Pr | B | 3290 2700 1610 | 57.94 5.92 5.88 / 58.24 5.98 5.86 |
| 10 | 5 | DMP | 29.4 | Colorless viscous | | | 3360 2990 1615 1592 | $C_{21}H_{26}N_2O_5 \cdot HCl$ |
|    |   |     |      | **155–157 | Pr | B | 3320 2750 1612 1593 | 59.64 6.44 6.62 / 59.58 6.51 6.90 |
| 11 | 6 | DMP | 67.3 | 116–118 | Pr | D | 3240 2750 1625 ** | $C_{23}H_{27}N_2O_9 \cdot HCl$ |
|    |   |     |      | *183–184 | Pr | E | 3310 2650 1623 | 57.97 5.92 5.88 / 57.64 6.02 5.91 |
| 12 | 7 | DMP | 83.9 | 106–108 | Pr | D | 3280 2760 1625 1607 | $C_{23}H_{28}N_2O_9$* |
|    |   |     |      | *155–157 | Pr | B | 3370 2800 1627 1607 | 57.97 5.92 5.88 / 57.44 6.01 5.84 |
| 13 | 4 | PhEᶠ | | 107–108 | Pr | F | 3300 3050 1618 | $C_{19}H_{22}N_2O_4 \cdot HCl$ |
|    |   |      | | *143–145 | Pr | G | 3320 2500 1616 | 60.24 6.12 7.39 / 60.15 6.30 7.31 |

Note
Ex. No., a and b are each as noted in Table 2.
c : Recrystallization solvent, B = ethanol, D = Benzene-hexane, E = methanol, F = benzene, G = methanol-ether
d : DMP = 3,4-dimethoxyphenethyl
f : PhE = phenoxyethyl
* : oxalate
** : hydrochloride

Table 4

| Ex. No. | R¹ | R² | A | a | Yield | M.P. (°C) Free Base Hydrochloride | b | c | IR $\nu_{max}^{Nujol}$ cm⁻¹ |
|---|---|---|---|---|---|---|---|---|---|
| 14 | Bu | i-Pr | H | 4 | 90.2 | 73–75 | Pr | A | 3255 3115 1617 |
|    |    |      |   |   |      | 134–136 | N | H | 3300 2700 1616 |
| 15 | Bu | t-Bu | H | 4 | 80.7 | 103–104 | Pr | A | 3300 3135 1617 |
|    |    |      |   |   |      | 145–146 | N | H | 3315 2780 1616 |
| 16 | i-Bu | t-Bu | H | 4 | 96.7 | 79–80 | Pr | A | 3290 3085 1618 |
|    |      |      |   |   |      | 133–134 | N | J | 3320 2720 1605 |
| 17 | Ph | t-Bu | H | 4 | 78.5 | 116–117 | Pr | D | 3280 3070 1618 |
|    |    |      |   |   |      | 210–212 | N | G | 3364 2770 1618 |
| 18 | Me | i-Pr | 7-Acetyl- | 4 | 94.7 | 153–154 | Pr | E | 3280 1695 |

Table 4-continued

| Ex. No. | R¹ | R² | A | a | Yield | M.P. (°C) Free Base Hydrochloride | b | c | IR $\nu_{max}^{Nujol}$ cm$^{-1}$ |
|---|---|---|---|---|---|---|---|---|---|
| | | | amino- | | | 225–227 | Pr | A | 3225 2550–2790 1663 |
| 19 | Me | t-Bu | 7-Acetyl amino | 4 | 94.1 | 185–187 | Pr | E | 3300 1695 |
| | | | | | | 224–225 | Pr | H | 3435 3200 2700 1668 |
| 20 | Me | t-Bu | 7-Cyclo-hexyl-ureido | 4 | 98.8 | 209–211 | Pr | E | 3300 3295 2700 1695 |
| | | | | | | 162–164 | Pr | H | 3300 3280 2670 1664 |
| 21 | Me | t-Bu | 7-Phenyl-ureido | 4 | 76.4 | 208–210 (d) | Pr | E | 3315 3290 2700 1710 |
| | | | | | | 230–232 | Pr | H | 3400 3305 2780 1711 |
| 22 | Me | i-Pr | 5-Me | 4 | 61.9 | 81–82 | Pr | A | 3290 3060 1610 |
| | | | | | | 153–155 | N | G | 3330 2500 1609 |
| 23 | Me | t-Bu | 5-Me | 4 | 94.2 | Viscous | | | 3365 3080 1608 |
| | | | | | | 211–212 | Pr | E | 3275 2700 1612 |
| 24 | Me | t-Bu | 5,7-Di-Me | 4 | 75.0 | 63–65 | Pr | A | 3280 3080 1617 |
| | | | | | | 216–218 | Pr | G | 3360 2350 1618 |
| 25 | Me | i-Pr | 5-Allyl | 4 | 97.3 | Viscous | | | 3350 3050 1640 1606 |
| | | | | | | 121–123 | Pr | I | 3250 2700 1641 1605 |
| 26 | Me | t-Bu | 5-Allyl | 4 | 91.3 | 89–90 | Pr | A | 3270 3050 1641 1608 |
| | | | | | | 144–146 | Pr | I | 3300 2760 1640 1605 |
| 27 | Me | PhE | 5-Allyl | 4 | 56.3 | Viscous | | | 3360 3040 1603 |
| | | | | | | 78–80 | Pr | J | — |
| 28 | Me | t-Bu | 5-Acetyl | 4 | 81.0 | Viscous | | | — |
| | | | | | | 212–213 | Pr | E | 3210 2740 1672 1605 |
| 29 | Me | t-Bu | 7-Acetyl | 4 | 84.5 | 170–171 | Pr | F | 3280 3100 1698 1612 |
| | | | | | | 247–248 | Pr | E | 3340 2700 1683 1618 |

Note:
Recrystallization solvents, H, I and J are acetone, acetone-ether and acetone-hexane, respectively; Me is methyl; Bu is butyl; Ph is phenyl; (d) is decomposition; and other marks and abbreviations are each as noted in Tables 2 and 3.

What we claim is:

1. A compound of the formula:

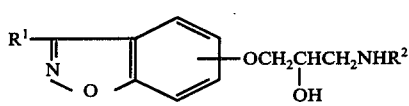

wherein
R¹ is methyl;
R² is isopropyl, tert-butyl, 3,4-dimethoxyphenethyl, or phenoxyethyl;
and the pharmaceutically acceptable acid-addition salts thereof.

2. A compound according to claim 1, wherein the group

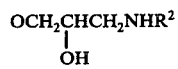

is located at 4 position.

3. A compound according to claim 1 wherein the group

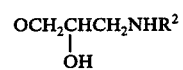

is located at the 7 position.

4. A compound according to claim 2, namely 3-methyl-4-(2-hydroxy-3-tert-butylaminopropoxy)-1,2-benzisoxazole.

5. A compound according to claim 2, namely 3-methyl-4-(2-hydroxy-3-isopropylaminopropoxy)-1,2-benzisoxazole.

6. A compound according to claim 3, namely 3-methyl-7-(2-hydroxy-3-tert-butylaminopropoxy)-1,2-benzisoxazole.

7. A compound according to claim 3, namely 3-methyl-7-(2-hydroxy-3-isopropylaminopropoxy)-1,2-benzisoxazole.

* * * * *